(12) United States Patent
Lins (10) Patent No.: US 7,674,429 B2
(45) Date of Patent: Mar. 9, 2010

(54) ELECTROSTATIC DISINFECTANT DELIVERY

(75) Inventor: Claudio L. K. Lins, Racine, WI (US)

(73) Assignee: JohnsonDiversey, Inc., Sturtevant, WI (US)

( * ) Notice: Subject to any disclaimer, the term of this patent is extended or adjusted under 35 U.S.C. 154(b) by 2380 days.

(21) Appl. No.: 09/766,730

(22) Filed: Jan. 22, 2001

(65) Prior Publication Data

US 2002/0155026 A1  Oct. 24, 2002

(51) Int. Cl.
*A61L 9/00* (2006.01)
*A61L 2/00* (2006.01)
*C23F 11/00* (2006.01)
*A62B 7/08* (2006.01)
*A61M 16/00* (2006.01)
*A01G 23/10* (2006.01)
*A01G 27/00* (2006.01)
*A24F 25/00* (2006.01)
*B05B 9/00* (2006.01)
*B01D 47/00* (2006.01)
*A61K 7/00* (2006.01)

(52) U.S. Cl. ............ 422/28; 422/1; 422/4; 422/5; 422/22; 422/123; 422/7; 422/120; 422/125; 422/305; 422/306; 422/307; 392/390; 392/395; 239/3; 239/34; 239/44; 239/60; 239/690; 239/145; 239/326; 239/706; 239/707; 261/75; 261/99; 261/100; 424/47; 424/76.8

(58) Field of Classification Search .......... 422/1, 422/4–5, 22, 28, 120–123, 125, 305–307, 422/7; 392/390, 395; 239/44, 3, 34, 60, 239/690, 706–707, 145, 326; 261/75, 99, 261/100; 424/47, 76.8
See application file for complete search history.

(56) References Cited

U.S. PATENT DOCUMENTS

| | | | | | |
|---|---|---|---|---|---|
| 4,071,616 | A | * | 1/1978 | Bloch | 424/76.4 |
| 4,083,954 | A | * | 4/1978 | Tsuchiya et al. | 424/47 |
| 4,400,332 | A | | 8/1983 | Pollard et al. | |
| 4,776,515 | A | | 10/1988 | Michalchik | |
| 4,829,996 | A | | 5/1989 | Noakes et al. | |
| 5,167,950 | A | * | 12/1992 | Lins | 424/47 |
| 5,196,171 | A | * | 3/1993 | Peltier | 422/121 |
| 5,382,410 | A | * | 1/1995 | Peltier | 422/121 |
| 5,405,602 | A | | 4/1995 | Simmons et al. | |
| 5,503,335 | A | | 4/1996 | Noakes et al. | |
| 5,591,395 | A | * | 1/1997 | Schroeder et al. | 422/4 |
| 5,810,265 | A | | 9/1998 | Cornelius et al. | |
| 6,105,877 | A | * | 8/2000 | Coffee | 239/3 |

(Continued)

FOREIGN PATENT DOCUMENTS

EP   0 486 198 A1   5/1992

(Continued)

OTHER PUBLICATIONS

Two internet print-outs for the definition of microSiemen.*

(Continued)

*Primary Examiner*—Jill Warden
*Assistant Examiner*—Monzer R Chorbaji
(74) *Attorney, Agent, or Firm*—Reinhart Boerner Van Deuren (57) ABSTRACT

Glycolic disinfectant compositions and related methods and apparatus for electrostatic dispensation.

21 Claims, 4 Drawing Sheets

U.S. PATENT DOCUMENTS 6,482,357 B1 * 11/2002 Fox et al. .................. 422/4
6,531,142 B1 * 3/2003 Rabe et al. .................. 424/401
6,880,554 B1 * 4/2005 Coffee .................. 128/200.14

FOREIGN PATENT DOCUMENTS

| EP | | 0 520 547 | A2 | | 12/1992 |
| NL | EP | 0 520 547 | A2 | * | 12/1992 |
| WO | | WO 95/02393 | A1 | | 1/1995 |

OTHER PUBLICATIONS

One internet print-out for the definition of centipoise.*
Two internet print-outs for the definition of microSiemen, 1996.*
One internet print-out for the definition of centipoise, 2003.*
United States Environmental Protection Agency. Efficacy Data and Labeling Requirements: Air Sanitizers. DIS/TSS-11, Sep. 3, 1980, pp. 1-5.

* cited by examiner

ELECTROSTATIC DISINFECTANT DELIVERY

BACKGROUND OF THE INVENTION

This invention relates generally to the use of glycolic compositions as airborne disinfectants and to the electrostatic delivery of such compositions to the environment.

It has been long known in the art that certain glycol compounds and compositions containing them can provide an air sanitation effect when appropriately dispersed. Although various regulatory guidelines are applicable, disinfecting compositions containing about 5 weight percent or more of the active glycol constituent are effective when dispensed into the environment at an adequate rate.

It has been known to use indirect heating of a wick as a method of dispensing various biocidal materials. In particular, U.S. Pat. No. 5,591,395 describes such methods and apparatus for disinfecting air with glycolic compositions. Therein, the method is described as immersing a portion of a porous wick in a liquid composition, then indirectly heating the top of the wick to generate airborne particles of the active disinfecting agent. Certain glycolic compounds readily provide particles, forming an aerosol suspension, at temperatures which can be safely employed in conjunction with apparatus described. The active particles are believed to be contact disinfectants, with respect to airborne bacteria and/or other discrete particulates present.

However, indirect heating methods are not without deficiencies. Various disinfectant compositions may present an undue flammability risk. The heat generated invariably raises ambient temperatures, a side effect counterproductive for an air-conditioned or otherwise temperature controlled environment. The resulting particle size may be difficult to control or ineffectual with respect to optimum sanitization.

The search for an efficient, effective delivery system has been an ongoing concern in the art. One approach, which has been used with some success, is as described in U.S. Pat. Nos. 5,196,171 and 5,382,410: the controlled generation of vapors and/or aerosols from liquids is accomplished by applying a regulated DC voltage to a wick-like, porous emitter or generator assembly supplied with a dispensable liquid. An electrostatic charge is applied to the liquid by means of an electrode positioned in contact with the wick assembly connected to a power supply. The wick assembly includes, preferably, a porous, capillary material through which the liquid passes to exposed, vapor-emitting fiber tips. Specific liquid formulations are left unaddressed by the '171 and '410 patents. Suitable liquids are described only generally as including those which may include disinfectant and/or fragrance agents which impart their respective properties upon delivery.

SUMMARY OF THE INVENTION

In light of the foregoing, one aspect of the present invention is to provide disinfectant compositions and/or systems and methods relating thereto, thereby overcoming the various deficiencies and shortcomings of the prior art, including those outlined above. In particular, it has now been found that formulations useful in conjunction with electrostatic systems require a minimal charge capacity for proper dispensation and desired effect. Compositions exceeding a certain water content do not maintain an electrostatic charge. Accordingly, glycolic compounds, hygroscopic by nature, and heretofore unsuitable for electrostatic delivery, are now provided in conjunction with the inventive compositions, systems and methods described herein.

Another aspect of the present invention is to provide a method of dispensing a disinfectant glycol composition without use of heat, thereby also providing the level of associated aerosol and/or vapor disinfectant sufficient to reduce airborne microorganism contaminants.

The present invention also provides a method and/or system for electrostatic delivery of glycol compositions, thereby permitting delivery and/or dispensation thereof at a rate sufficient to sanitize airborne contaminants. The present invention makes use of an alcohol component to enhance the electrostatic dispersion of a glycol disinfectant.

It has been discovered that a wide range of glycol compositions which can be used with comparable effect in conjunction with a variety of commercially-available electrostatic dispensing units, without significant redesign, configuration or modification.

A concurrent advantage of the present invention is that it provides disinfectant compositions without the presence of substantial aqueous component which would otherwise facilitate the growth and proliferation of microorganisms, in direct contravention of various aforementioned goals and objectives.

Other aspects, objects, benefits, features and/or advantages of the present invention will be apparent from this summary and the following descriptions of various preferred embodiments, and will be readily apparent to those skilled in the art having knowledge of various disinfectant compositions and electrostatic delivery systems. Such objects, features, benefits and advantages will be apparent from the above as taken into conjunction with the accompanying examples, data, figures and all reasonable inferences to be drawn therefrom, alone or with consideration of the references incorporated herein.

DETAILED DESCRIPTIONS OF PREFERRED EMBODIMENTS

The disinfectant compositions of the present invention are substantially non-aqueous and include an alcohol solvent component and a glycol solute component. The inventive compositions are, surprisingly, electrostatically dispensable. Various alcoholic components can be employed, so long as the glycol component is sufficiently solvated and/or dispersed and a sufficiently homogeneous composition is thereby provided for subsequent use. Accordingly, in preferred embodiments of this invention, the solvent component can include but is not limited to ethanol, isopropanol, benzyl alcohol and/or combinations thereof.

Further, with respect to those preferred embodiments, the alcohol component can comprise about 10 weight percent to about 80 weight percent of the inventive composition. Aside from the aforementioned solvation, the amount of alcohol utilized can vary depending upon several factors including choice of glycol and other components present. Regardless, the identity and amount of alcohol can be used to provide compositional viscosities of the sort useful for electrostatic delivery. Preferred compositions of the present invention have a viscosity between about 0.1 centipoise (at 20° C.) to about 50 centipoise. Optimally, depending upon glycol identity and desired delivery rate, the composition has a viscosity of about 5 centipoise to about 10 centipoise.

The aforementioned alcohols, as well as other such solvent components contemplated herein, are available as or readily form azeotropic mixtures with water. The aqueous component of such azeotropes is present at or up to a weight or volume percent well known to those skilled in the art. Without restriction to any one theory, mechanism or mode of operation, it is within the scope of this invention that the alcohol component of the present compositions can control or otherwise affect the amount of water therein, thereby providing a counter to the hygroscopic nature of the glycol component and enhancing the electrostatic dispensation of the resulting composition.

Preferred compositions of the present invention can further include a conductivity control component present in an amount sufficient to provide the composition a conductivity of about 0.01 microsiemens per centimeter to about 1.0 microsiemens per centimeter. In various preferred embodiments, the conductivity control component is one of several fragrance components, each of which can be present at about 10 weight percent to about 90 weight percent of the composition. Such components can include, but are not limited to, those commercially available from Robertet Fragrances, Inc. of Oakland, N.J. under the M-82, SM-96 and/or TF-69 trade designations. Various essential oils, silicon oils and/or other aliphatic materials can also be used with good effect. Alternate conductivity control components include various fatty acid esters, such as but not limited to the alcohol esters of palmitic and myristic acids. Such control agents, employed as described herein, can lower conductivity and provide an electrostatic delivery rate sufficient for the required reduction of airborne bacterial levels.

A variety of glycols can be used in conjunction herewith, the choice of which limited only by the desired antiseptic effect. Accordingly, the glycol component of this invention can be, but is not limited to, propylene glycol, dipropylene glycol, triethylene glycol and combinations thereof. Preferably, such a glycol component is present at about 5 weight percent to about 80 weight percent of the composition. As described herein, an especially effective disinfectant is one which includes triethylene glycol.

In part, the present invention can also provide a substantially non-aqueous disinfectant composition including (1) a glycol component present at about 5 weight percent to about 20 weight percent; (2) an alcohol component present at about 30 weight percent to about 70 weight percent; and optionally (3) a conductivity control component present at about 15 weight percent to about 50 weight percent, such component present in an amount sufficient to provide the composition a conductivity from about 0.01 microsiemens per centimeter to about 1.0 microsiemens per centimeter. As described above, such a disinfectant composition can include triethylene glycol and ethanol, each component within a range of weight percents such that the resulting composition has a viscosity of about 0.1 centipoise to about 50 centipoise. Regardless of the glycol or alcohol components, the conductivity control component can be, but is not limited to, a silicon oil, an essential oil and/or a fatty acid ester. Various other aliphatic materials can be used with equal effect. In preferred embodiments, the conductivity control component is an essential oil present in an amount sufficient to provide the composition a conductivity of about 0.1 microsiemens per centimeter to about 0.2 microsiemens per centimeter.

In part, the present invention can also provide a system for electrostatic delivery of an antimicrobial material. Such a system can include (1) a disinfectant composition including a glycol component, an alcohol component and a conductivity control component; and (2) an apparatus for generating an electrostatic charge and imparting the charge to the disinfectant composition. Consistent with the broader aspects of this inventive system, such an apparatus can have an electrode conductively connected to a voltage source and a dispenser providing the disinfectant composition in sufficient proximity to the electrode to permit electrostatic charging of the disinfectant. Preferred embodiments of this system include apparatus selected from those described in the aforementioned U.S. Pat. Nos. 5,196,171 and 5,382,410, each of which is incorporated herein by reference as described below.

The glycol component of the inventive composition is delivered in an amount sufficient to provide a three-log reduction in airborne microbial levels within a time period prescribed by accepted protocols. Alternatively, such a system can be used as a prophylactic measure to keep bacterial levels low and/or within acceptable limits. The glycol component is present at solute concentrations within one or more of the alcohol components described above. Good efficacy can be achieved when the resulting disinfectant composition is electrostatically delivered at a rate of at least 0.1 grams per hour and preferably at least 0.3 g rams per hour.

As such, the present invention can also be directed to a method of using a glycol to reduce airborne microbial levels. Such a method includes (1) providing an electrostatically dispensable glycol composition; (2) charging the glycol composition with an apparatus including an electrode conductively connected to a voltage source; and (3) dispensing the charged glycol composition in an amount and at a rate sufficient to effect a three-log reduction in airborne microbial levels. As described above, the glycol composition includes an alcohol soluble glycol such as but not limited to propylene glycol, dipropylene glycol, triethylene glycol and combinations thereof. In preferred embodiments, the glycol is triethylene glycol, and the dispensation rate of the alcoholic composition is greater than about 0.1 grams per hour and preferably 0.3 grams per hour or more. Such a rate can be achieved and/or enhanced by inclusion of a conductivity control component present in an amount to provide such a preferred composition a conductivity of about 0.1 microsiemens per centimeter to about 1.0 microsiemens per centimeter.

As mentioned above, the use of glycol compositions as air disinfectants has been previously considered solely in the context of indirect heating for generation of airborne particles. Compositional viscosity is of no concern in such applications, and use of water as a preferred solvent discounts any control or limitation on the conductivity of such compositions delivered electrostatically. In fact, inhaler technologies encourage relatively high viscosity and conductivity parameters.

Figure 1A:
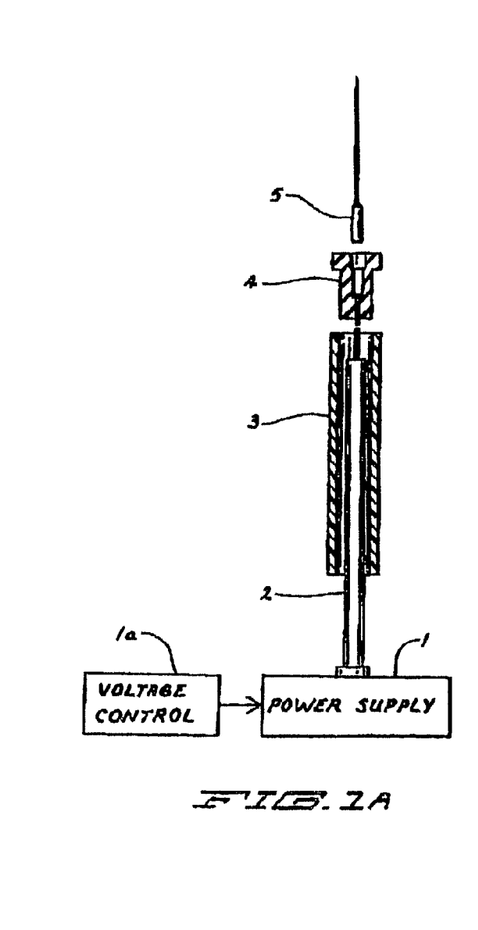
FIG. 1A shows, in accordance with this invention, a basic embodiment of the concept of the use of electrostatic charge to dispense/deliver a liquid of disinfectant of the type described herein.
Figures 1B, 1D:
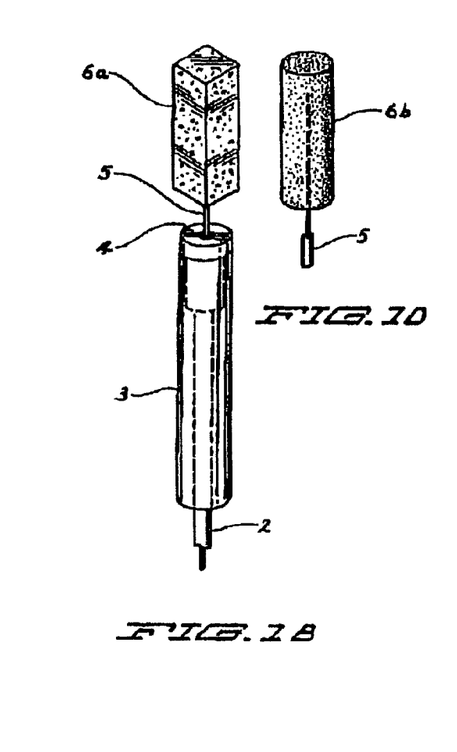
FIGS. 1B-1D show different wick embodiments.
Figure 1C:
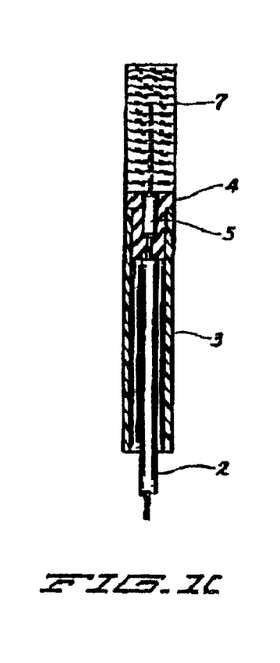
Figure 2:
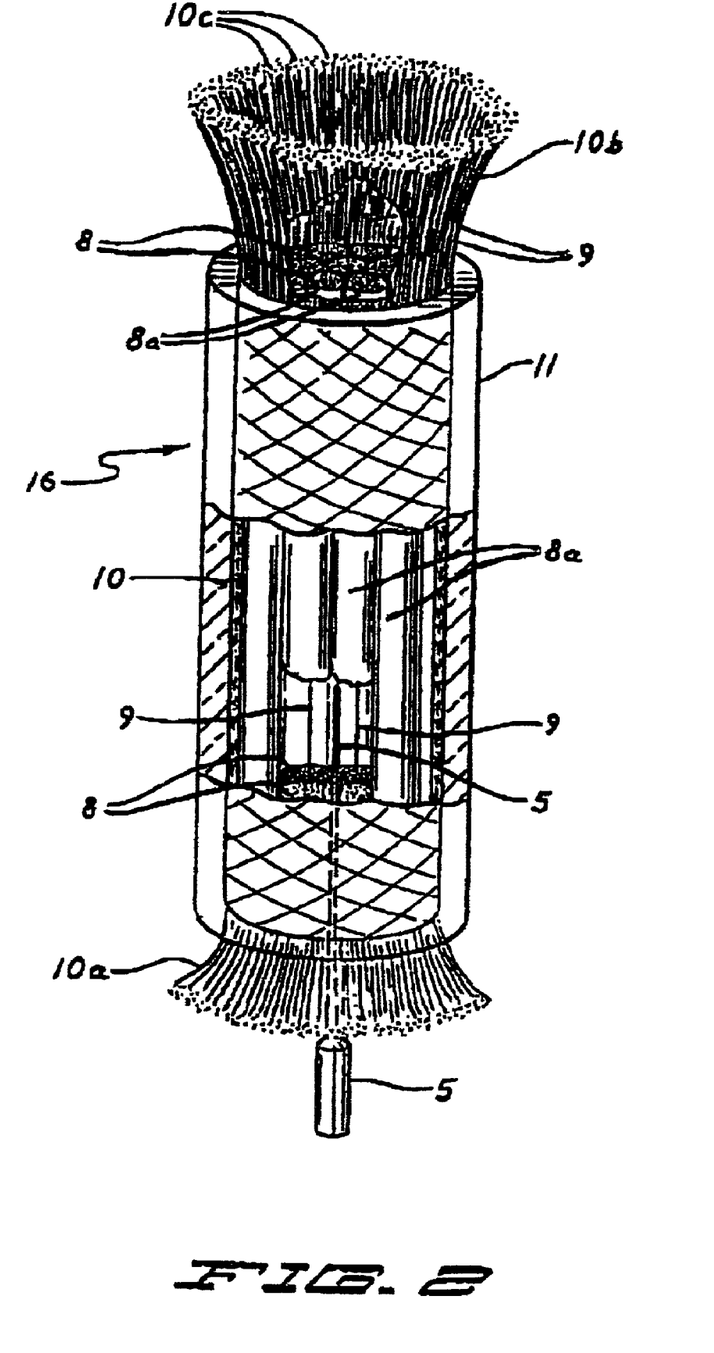
FIG. 2 is a perspective view of a preferred embodiment of a wick assembly partially in section.
Figure 3:
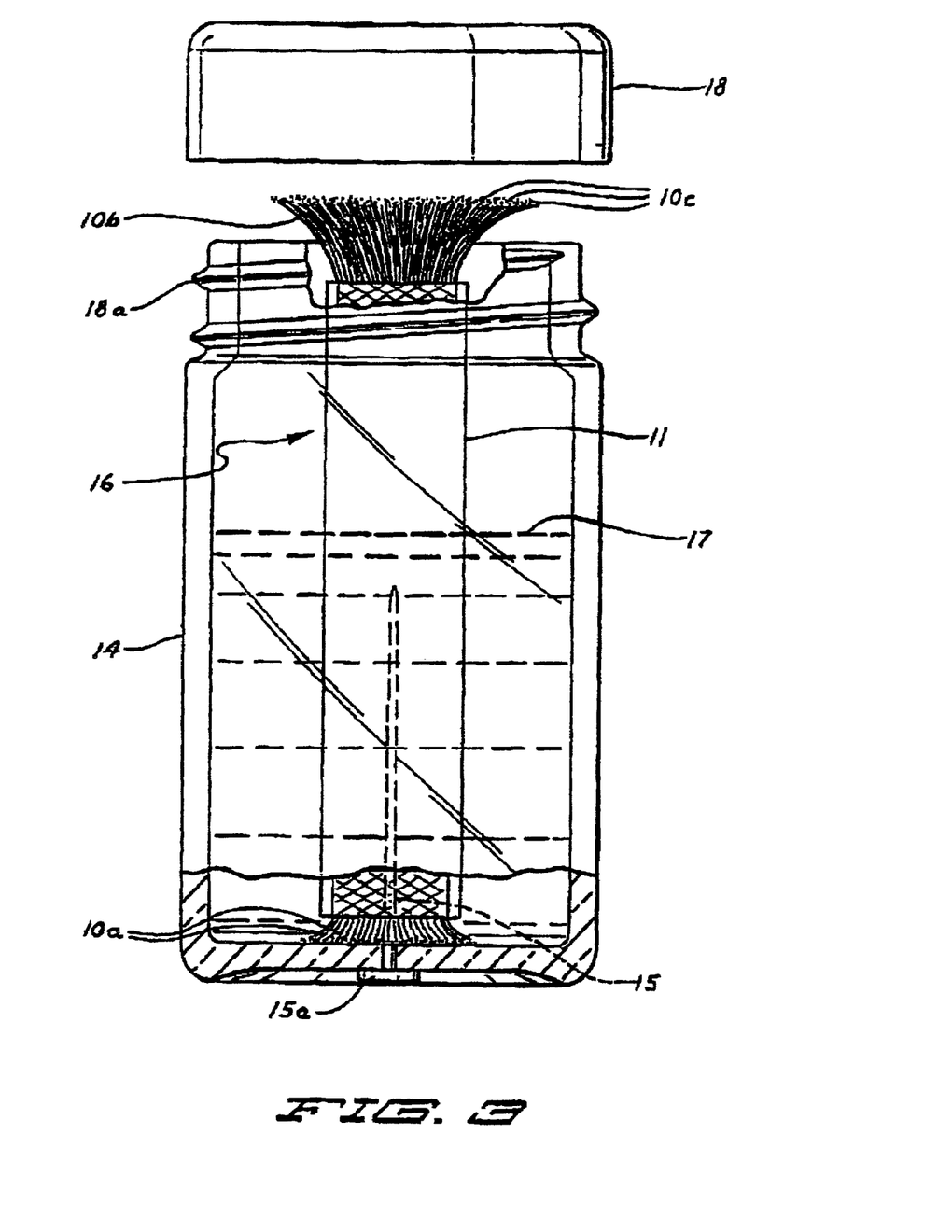
FIG. 3 shows the installation of the wick assembly shown in FIG. 2 within a glass bottle. This embodiment is a self-contained liquid storage and vapor/aerosol dispensing device.

Contrary to the prior art compositions, the disinfectants of the present invention require compositional components imparting relatively low viscosities and/or conductivities, the combination of which provides a delivery rate which ensures sufficient reduction in airborne microbial counts. Notwithstanding optimal parameter ranges disclosed elsewhere herein, the disinfectant compositions of this invention can have viscosity (generally less than 5 cps) and conductivity (generally less than 1.0 uS/cm) parameters sufficient to provide a minimum delivery rate of about 0.1 grams of composition per hour. Lower delivery rates are problematic with regard to sufficient microbial reduction within a reasonable time and/or maintenance of such reduced levels.

The compositions of this invention can be delivered electrostatically using any one of a number of commercially-available apparatus and/or device configurations. Especially suitable apparatus are described in U.S. Pat. Nos. 5,196,171 and 5,382,410—in particular the figures and corresponding text thereof—each of which is incorporated by reference in its entirety.

In one embodiment of such a device, a high voltage DC power supply with an adjustable output (5-50 kilovolts negative) can be used to power an "electrostatic wick" assembly which is comprised of a central conductive electrode, an outer porous capillary material, and a vial, vessel, or tubular enclosure used to contain and direct the liquid disinfectant composition. If the liquid is supplied to the apparatus by the use of a tube or pipe and if there is no requirement to "wick" the liquid, then the device is referred to as a "vaporizing emitter." In both devices the main components of the wick or emitter can be summarized as an electrostatically charged, liquid-fed, semi-conductive, porous, capillary assembly.

These "wicks" and "emitters" can be fabricated from the following materials, in a variety of combinations, in order to obtain the best vapor/aerosol generation performance for the liquid composition and also the optimum air output: conductive foam, ceramic fibers, graphite fibers, porous ceramic, porous polyethylene foam, porous sintered metals (discs, tubes, spheres, and sheets of stainless steel and brass), glass wool, fiberglass braiding, graphite braiding, stainless steel braiding, class tubing, polycarbonate tubing, wood wicking, wool felts, and other materials used alone and in combination.

In a further embodiment, a high voltage, DC power supply with a fixed or adjustable output (5-50 kilovolts negative) can be used to power a "vaporizing emitter" assembly which is comprised of a nonconductive tubular support over which is placed at one end an emitter sleeve comprised of a combination of fibers interwoven in a ribbonlike configuration to form bundles of distinct capillaments longitudinally oriented and freely extending at their terminal ends beyond the end of the support tubing. The freely extending terminal ends of the capillament bundles serve as charged vapor discharge sites. Preferably, the terminal ends of the capillament bundles assume brushlike configurations of distinct bundles of fibers which, if viewed at their ends, comprise dozens or hundreds of small bristle groups.

The aforesaid fibrous assembly can be comprised primarily of nonconductive materials. Distinct conductive fibers or wires may be optionally interwoven with the nonconductive fibers to serve as an aid to the transfer of an electrostatic charge to the ends of the capillament bundles. An electrode is placed in conductive relation to the aforesaid emitter sleeve, either directly, or by way of contact with an inner sleeve which may facilitate wicking of liquid to the emitter sleeve. A selected disinfectant composition is supplied to the aforesaid assembly from tubing by way of a fluid control system incorporating a supply pump.

These charged wicks or emitters directly effect the natural vapor pressure of any liquid which is applied to them at any given temperature and atmospheric pressure by using electrostatic forces acting upon the surface tension of the liquid held within a porous mass, wicking, or emitter assembly.

Advantageously, the aforesaid emitter assembly may be supported within an air duct of the central, air handling system for a building so as to discharge conditioning, charged vapors directly into the circulating air stream. In a preferred embodiment this is done by a support conduit extending through the wall of a duct, with the conduit also beneficially serving to carry the high voltage conductor lead and a liquid supply tube directed to the emitter assembly.

Referring to the aforementioned incorporated '410 and '171 patents, together with the accompanying texts, FIG. 1A illustrates, in exploded view, an embodiment of the "electrostatic wick" assembly and its power source, of the type which can be used in conjunction with the present invention. A high voltage DC power supply 1 with an adjustable output 1*a* (5-50 kilovolts negative 2-200 microamps) supplies power to a terminal 4 via a high voltage wire conduit 2. An electrode/charging element 5 is inserted in the terminal and provides the charge to the wick assemblies. High voltage terminal 4 is inserted into a plastic, e.g., polycarbonate, tube 3 as a support.

FIG. 1B is a view of these components fully assembled. The electrode is inserted into the wick material or assembly 6*a*, the desired disinfectant composition is supplied to the wick and power is applied at the desired voltage. The properties of the materials that comprise the wick have a significant effect upon the vapor and/or aerosol output efficiency at any given voltage setting. The porosity, conductance, and shape of the materials will determine the vapor-aerosol ratio.

In FIG. 1B the wick material 6*a* is a conductive, carbon-treated foam, which is saturated with the desired liquid composition and charged by the power supply 1. In this embodiment of the dispenser wick, the foam emanates a very strong vapor from all exposed surfaces with the greatest concentration coming from the corners and edges. Wick dispenser 6*b* as shown in FIG. 1D is comprised of porous sintered metal. A variety of shapes and metal types were saturated with liquid and placed onto the electrode. As with the carbon foam, they also generated vapor with the greatest concentration coming from the corners and edges. This follows the general rule that corona discharge will form at points or sharp radius edges. The liquid that is near these areas is carried away by this discharge forming a charged vapor.

FIG. 1C shows an embodiment of the same electrode support as in FIG. 1B with a wick 7 that is fabricated from a nonconductive porous material such as wool felt, porous polypropylene or similar material. The wick material is saturated with the desired aromatic liquid. The electrode is preferably inserted into the wick so that the entire electrode is covered by the wick. In this embodiment, the wick must conduct the full charge that is supplied to the electrode. The liquid disinfectant composition provides a means of conducting the charge from the center of the wick to the outer surfaces where vaporization take place in the same manner as the wicks that are conductive. This embodiment requires a higher voltage to generate the same amount of vapors as the wicks described in FIG. 1B.

FIG. 2 details a modified design of a wick or emitter assembly in comparison to the wicks shown in FIG. 1. Wick assembly 16 is comprised of a center electrode assembly which is made of ceramic fibers 8 in which are embedded stainless steel wires 9. Fibers 8 are preferably formed into a plurality of elongated capillament bundles 8*a* as shown. The fibers 8 may be braided or twisted, with wires 9 either extending straight therein or intertwined with the fibers. This design also is a very effective air ion emitter. This illustration is an example of the concept of using a number of materials which together have the desired properties of porosity, conductance, and capillary action, and will generate vapor and/or aerosols when electrified by a voltage high enough to break the surface tension of the desired liquid.

FIG. 3 is a preferred embodiment of a device that will also provide a means of containing the liquid disinfectant that would be supplied to the wick assembly 16 of FIG. 2. In this embodiment a bottle/reservoir 14 contains the wick dispenser assembly 16 and has a high voltage electrode/charging element 15 which extends through the bottom of the bottle. It also has a contact terminal 15a on the bottom of the bottle in order to provide a means of supplying a charge to the wick assembly 16. The desired composition 17 is contained within the bottle and is continuously moved to the top of the wick by capillary action. That action is enhanced by the extension of fiber end segments 10a into the liquid at the lower end of wick assembly 16. The bottle can be sealed by a cap 18 and stored for later use without loss of liquid due to evaporation or spilling. This embodiment is a self-contained system that will generate vapor and/or aerosols and also air ions when it is provided a high voltage DC signal to the base electrode and the bottle cap 18 is removed. A threaded cap 18 may be used for attachment to threads 18a on bottle 14.

Figure 4:
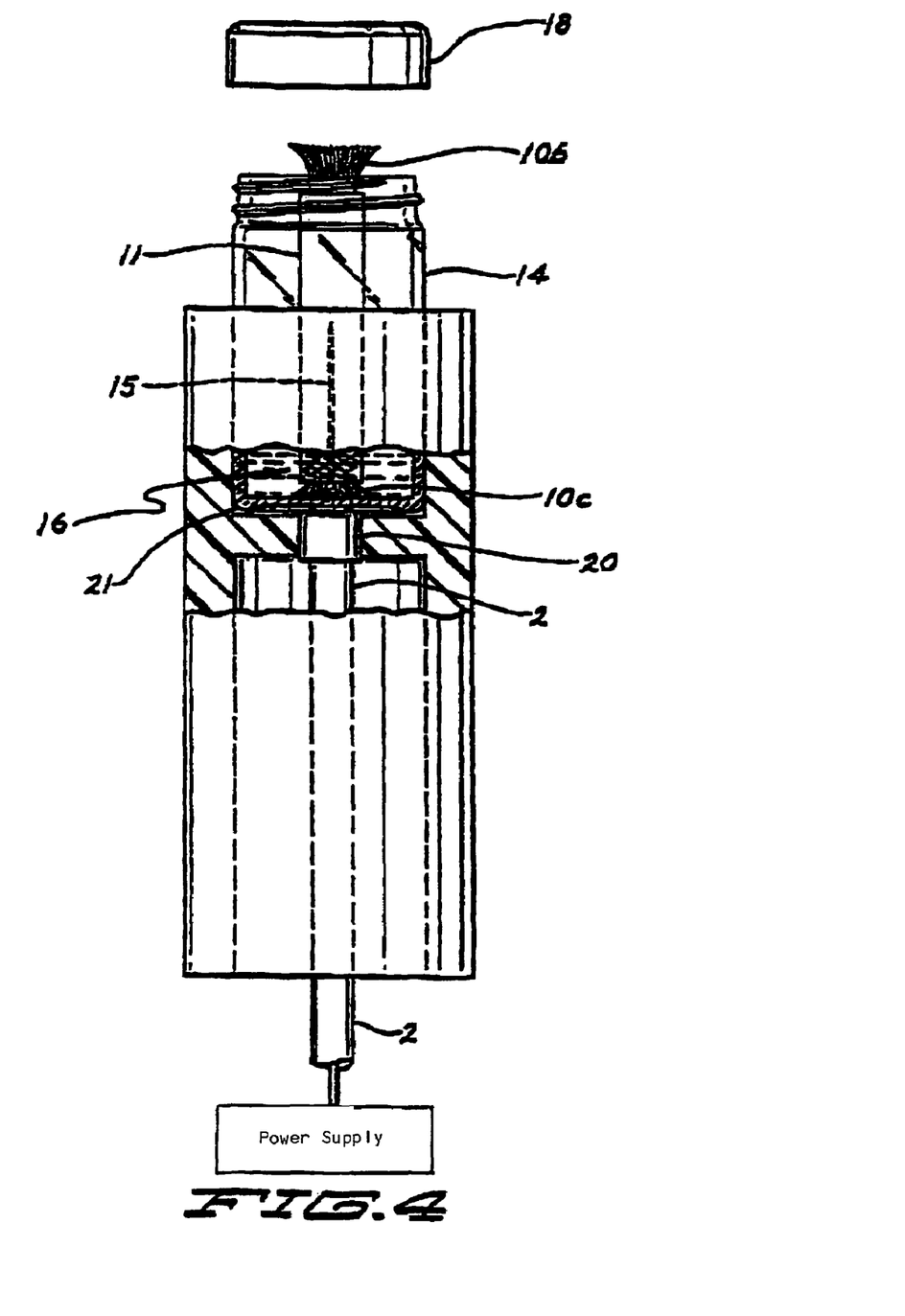
FIG. 4 shows an embodiment of an apparatus to contain a liquid, and dispense an aerosol/vapor thereof by application of an electrostatic charge to it.

FIG. 4 shows an embodiment of a device that holds the vaporizing bottles detailed in FIG. 3. The device comprises an insulating support column made of porcelain, glass, plastic or a similar such material. A high voltage DC signal is supplied to the contact terminal connector 20 by a high voltage wire 20. The electrode contact 15a (shown in FIG. 3) of bottle 14 makes contact with the power contact 20 as shown. This provides power to the wick assembly 16 and causes the vapor and/or aerosols to emanate from the top of the bottle into the adjacent atmosphere. The bottle 14 is secured within the recess 21 of the aforementioned support column.

Each of FIGS. 1-4 can be modified as would be well-known to those skilled in the art to discharge vapor/aerosol directly into a room space or to indirectly condition the atmosphere of one or more rooms by discharge into a vent or duct structure of a building air handling system. Such modifications can include various other embodiments of the type illustrated in the figures of aforementioned '410 and '171 patents, as explained more fully in the accompanying texts, all of which are incorporated herein by reference.

Using devices of the sort described above, electrostatically charged vapor and/or aerosol may be dispensed into ambient air and/or the air handling system of a building as described above to odorize by the use of essential oils or perfumes and/or to sanitize by the use of biocides such as fungicides, bactericides, fumigants, insecticides, disinfectants, and the like. In this manner, micro-organisms such as bacteria, fungus, mold, and the like present in room atmospheres or which collect in air handling and air conditioning systems, and particularly on the surfaces of ducts and air handling equipment, may be treated, neutralized and/or controlled.

EXAMPLES OF THE INVENTION

The following non-limiting examples and the data illustrate various aspects and features relating to the compositions/systems and/or methods of the present invention, including the electrostatic delivery system for various disinfectant compositions described herein. In comparison with the prior art, the present methods and compositions/systems provide results and data which are surprising, unexpected and contrary to the prior art. While the utility of this invention is illustrated through use of several articles, systems and/or devices and the disinfectant compositions which can be used therewith, it will be understood by those skilled in the art that comparable results are obtainable with various other articles, systems or devices and disinfectant compositions, as are commensurate with the scope of this invention.

Various disinfectant compositions were measured to determine associated viscosity, conductivity and/or delivery rate parameters. Viscosity measurements were conducted with a Brookfield DV-III rheometer using procedures well known to those skilled in the art. Conductivity measurements were taken using a conductivity meter (Accumet Basic AV30) instrument using a two cell conductivity probe (epoxy body with a cell constant of 1.0). Delivery rates were determined with a preferred electrostatic delivery apparatus, available through In-Vironmental Integrity, Inc. of Minneapolis, Minn. under the "Aromasys" trademark using standard procedures and protocols.

Example 1

Initial viscosity (51.5 cps), conductivity (0.354 uS/cm) and delivery rate (−0.102 grams/hour) were determined as a point of reference for triethylene glycol, a glycol component typical of the present invention. The negative delivery rate measured represents a mass gain over the test period, presumably due to water absorption and thereby confirming the convention that such materials are unsuitable for charged electrostatic delivery.

In comparison, Examples 2-15, below, show similar determinations made for various compositions prepared using a glycol and other such components of the type described herein. (Triethylene glycol, TEG; Dipropylene glycol, DG; Butyl glycol, BG; Ethanol, EtOH; Isopropanol, IPA; Benzyl alcohol, BA; SM-96, TF-69, and RM-82—commercial fragrances).

Example 2

| Component | % (wt.) |
| --- | --- |
| TEG | 10 |
| EtOH | 80 |
| SM-96 | 10 |

Delivery rate, 0.708 gms/hr; viscosity 35.5 cps; and conductivity, 2.0 uS/cm.

Example 3

| Component | % (wt.) |
| --- | --- |
| TEG | 10 |
| EtOH | 60 |
| SM-96 | 30 |

Delivery rate, 0.474 gms/hr; viscosity 21.8 cps; and conductivity 1.25 uS/cm.

Example 4

| Component | % (wt.) |
| --- | --- |
| TEG | 10 |
| EtOH | 40 |
| SM-96 | 50 |

Delivery rate, 0.2628 gms/hr; viscosity 7.72 cps; and conductivity 0.801 uS/cm.

Example 5

| Component | % (wt.) |
|---|---|
| TEG | 10 |
| EtOH | 10 |
| SM-96 | 80 |

Delivery rate, 0.09 gms/hr; viscosity 13 cps; and conductivity 0.275 uS/cm.

Example 6

| Component | % (wt.) |
|---|---|
| TEG | 13.36 |
| EtOH | 56.32 |
| RM-82 | 30.32 |

Delivery rate, 0.3996 gms/hr; viscosity 3.46 cps; and conductivity 0.115 uS/cm.

Example 7

| Component | % (wt.) |
|---|---|
| TEG | 13.36 |
| EtOH | 56.32 |
| TF-69 | 30.32 |

Delivery rate, 0.528 gms/hr.

Example 8

| Component | % (wt.) |
|---|---|
| PG | 13.36 |
| EtOH | 56.32 |
| TF-69 | 30.36 |

Delivery rate, 0.4284 gms/hr.

Example 9

| Component | % (wt.) |
|---|---|
| BG | 13.36 |
| EtOH | 56.32 |
| TF-69 | 30.32 |

Delivery rate, 0.4932 gms/hr.

Example 10

| Component | % (wt.) |
|---|---|
| TEG | 13.36 |
| IPA | 56.32 |
| TF-69 | 30.32 |

Delivery rate, 0.45 gms/hr.

Example 11

| Component | % (wt.) |
|---|---|
| PG | 13.36 |
| IPA | 56.32 |
| TF-69 | 30.32 |

Delivery rate, 0.3972 gms/hr.

Example 12

| Component | % (wt.) |
|---|---|
| BG | 13.36 |
| IPA | 56.32 |
| TF-69 | 30.32 |

Delivery rate, 0.4836 gms/hr.

Example 13

| Component | % (wt.) |
|---|---|
| TEG | 25 |
| EtOH | 75 |

Delivery rate, 0.675 gms/hr; viscosity, 2.91 cps; and conductivity, 2.168 uS/cm.

Example 14

| Component | % (wt.) |
|---|---|
| TEG | 50 |
| EtOH | 50 |

Delivery rate, 0.368 gms/hr; viscosity, 7.8 cps; and conductivity, 1.355 uS/cm.

Example 15

| Component | % (wt.) |
|---|---|
| TEG | 75 |
| EtOH | 25 |

Delivery rate, 0.12 gms/hr; viscosity, 14.8 cps; and conductivity 0.915 uS/cm.

Example 16

The components of this example can be formulated as follows to provide disinfectant properties of the sort described elsewhere herein.

| | Glycol (wt. %) | Alcohol (wt. %) | Conductivity Control Agent (wt. %) |
|---|---|---|---|
| a | TEG (50%) | EtOH (25%) | SM-96 (25%) |
| b | TEG (75%) | EtOH (15%) | SM-96 (10%) |

Such compositions and variations thereof, in accordance with this invention, have viscosity and/or conductivity properties such that they can be electrostatically delivered at rates greater than 0.1 grams per hour and/or comparable to those described elsewhere herein.

Example 17

The composition of Example 6 was tested in conjunction with a commercially-available Aromasys™ electrostatic dispenser unit. The unit was placed in a room with the temperature and humidity controlled to 25° C. and 35% RH. The room also was equipped with a Mattson-Garvin 220 slit to agar impingement sampler, which measures the number of colonies of bacteria over time. The composition of Example 6 (7.25 gm) was delivered into the room over a 26-hour period under the aforementioned temperature and humidity controlled conditions. An airborne bacterium, Micrococcus luteus was then introduced into the room. Air samples were taken after 1-2, 6-7, 11-12, 16-17, 21-22 and 26-27 minutes. In addition, a controlled room test, without introduction of any disinfectant, was conducted using the same procedure. The results are as provided in Table 1, and demonstrate the utility of the present compositions, systems and/or methods by way of statistically eliminating airborne bacteria within a reasonably limited period of time.

TABLE 1

| Time in Minutes | 1-2 | 6-7 | 11-12 | 16-17 | 21-22 | 26-27 |
|---|---|---|---|---|---|---|
| Example 6 | 660 | 11 | 9 | 0 | 0 | 0 |
| Control | 2180 | 1740 | 1475 | 1360 | 1280 | 1250 |

While the principles of this invention have been described in connection with specific embodiments, it should be understood clearly that these descriptions are added only by way of example and are not intended to limit, in any way, the scope of this invention. For instance, while benzyl alcohol can be problematic in the electrostatic delivery of certain associated glycol compositions, mixtures thereof with various other alcohol components can provide for effective delivery in conjunction with the antiseptic properties otherwise available through use of benzyl alcohol. Other advantages, features and benefits will become apparent from the claims hereinafter, with the scope of such claims as determined by the reasonable, available equivalents and as understood by those skilled in the art.

I claim:

1. A substantially non-aqueous electrostatically dispensable disinfectant composition comprising an alcohol solvent component in combination with a glycol solute component, said combination having an initial conductivity, and further comprising a conductivity control component comprising at least one of a silicon oil, an essential oil, a fatty acid ester and combinations thereof in an amount sufficient to reduce said initial conductivity, and wherein all composition components of the disinfectant composition for electrostatic dispensing are at least one of soluble and miscible.

2. The composition of claim 1 wherein said alcohol component is selected from the group consisting of ethanol, isopropanol, benzyl alcohol and combinations thereof.

3. The composition of claim 1 wherein said conductivity control component is present in an amount effective to provide said composition a conductivity of about 0.01 microsiemens per centimeter to about 1.0 microsiemens per centimeter.

4. The composition of claim 3 wherein said conductivity control component is present at about 10 weight percent to about 90 weight percent of said composition.

5. The composition of claim 1 wherein said glycol component is selected from the group consisting of propylene glycol, dipropylene glycol, triethylene glycol and combinations thereof, said glycol component present at about 5 weight percent to about 80 weight percent of said composition.

6. The composition of claim 5 wherein said glycol component is triethylene glycol.

7. The composition of claim 6 wherein said alcohol component is selected from the group consisting of ethanol, isopropanol, benzyl alcohol and combinations thereof, said alcohol component present at about 10 weight percent to about 80 weight percent of said composition.

8. The composition of claim 7 wherein said alcohol component is ethanol, present in an amount sufficient to provide said composition a viscosity of about 0.1 centipoise to about 50 centipoise.

9. A substantially non-aqueous disinfectant composition, said composition comprising:

a glycol component present at about 5 weight percent to about 20 weight percent;

an alcohol component present at about 30 weight percent to about 70 weight percent;

a conductivity control component present at about 15 weight percent to about 50 weight percent, said control component present in an amount sufficient to provide said composition a conductivity from about 0.01 microsiemens per centimeter to about 1.0 microsiemens per centimeter;

a balance of an aqueous component in an amount sufficient to form an azeotropic mixture with said alcohol component, wherein the electrostatically dispensable disinfectant composition is free of immiscible and insoluble topical composition particulates.

10. The composition of claim 9 wherein said glycol component is triethylene glycol and said alcohol component is ethanol, said composition having a viscosity of about 0.1 centipoise to about 50 centipoise.

11. The composition of claim 9 wherein said conductivity control component is selected from the group consisting of silicon oils, essential oils, fatty acid esters, aliphatic materials and combinations thereof.

12. The composition of claim 11 wherein said conductivity control component is an essential oil present in an amount sufficient to provide said composition a conductivity of about 0.1 microsiemens per centimeter to about 0.2 microsiemens per centimeter.

13. A system for electrostatic delivery of an antimicrobial material, said system comprising:
a disinfectant composition comprising a glycol component in combination with an alcohol component, said combination having an initial conductivity and a conductivity control component comprising at least one of a silicon oil, an essential oil, a fatty acid ester and combinations thereof, said conductivity control component present in an amount sufficient to reduce said initial conductivity of said combination; and
an electrostatic dispensing apparatus containing said disinfectant composition in a liquid reservoir, said apparatus further including an electrostatic charging element, a voltage source electrically connected to said element, and a dispenser providing said disinfectant composition in proximity to said element, said proximity sufficient to electrostatically charge said composition, wherein the electrostatic dispensing apparatus is at least one of an electrostatic wick and a vaporizing emitter, the electrostatic dispensing apparatus when subject to an electrical power source dispensing the disinfectant composition in a vapor and/or aerosol suspension form;
Wherein said glycol component is present at solute concentrations in said alcohol; and wherein said glycol is triethylene glycol and said composition is delivered at a rate of at least 0.1 grams per hour.

14. A method of using a glycol disinfectant composition to reduce airborne microbial levels, said method comprising:
providing an electrostatically dispensable, substantially non-aqueous glycol disinfectant composition comprising an alcohol solvent component in combination with a glycol solute component, said combination having an initial conductivity, and further comprising a conductivity control component comprising at least one of a silicon oil, an essential oil, a fatty acid ester and combinations thereof in an amount sufficient to reduce said initial conductivity;
charging said glycol disinfectant composition with an apparatus comprising only-one electrode conductively connected to a voltage source; and
dispensing said charged glycol disinfectant composition in an amount and at a rate sufficient to effect a 3-log reduction in airborne microbial levels.

15. The method of claim 14 wherein said glycol composition comprises a glycol dissolved in an alcohol, said glycol selected from the group consisting of propylene glycol, dipropylene glycol, triethylene glycol and combinations thereof.

16. The method of claim 15 wherein said glycol is triethylene glycol, and said dispensation rate is greater than about 0.1 grams per hour.

17. The method of claim 14 wherein said glycol composition includes a conductivity control component present in an amount sufficient to provide said composition a conductivity of about 0.01 microsiemens per centimeter to about 1.0 microsiemens per centimeter.

18. The method of claim 14, further comprising forming said charged glycol disinfectant composition into the aerosol and/or vapor within an air duct of a central air handling system of a building.

19. A substantially non-aqueous disinfectant composition, said composition comprising:
triethylene glycol present at about 10 weight percent to about 15 weight percent of said composition, said glycol having an initial viscosity and an initial conductivity;
ethanol present at about 45 weight percent to about 60 weight percent of said composition, said ethanol present in an amount sufficient to dissolve said glycol, said amount further sufficient to reduce said initial viscosity; and
a fragrance component present at about 20 weight percent to about 40 weight percent of said composition, said fragrance present in an amount sufficient to reduce said initial conductivity,
said composition electrostatically dispensable, having a viscosity and a conductivity sufficiently reduced to deliver said composition at a rate of at least about 0.1 grams per hour to about 0.5 grams per hour, and wherein all composition components of the disinfectant composition for electrostatic dispensing are at least one of soluble and miscible.

20. The composition of claim 19 wherein said ethanol solvent and said fragrance component are present in amounts sufficient to deliver said composition at a rate of about 0.3 grams per hour.

21. The composition of claim 20 wherein said triethylene glycol is present at about 13 weight percent of said composition, said ethanol is present at about 56 weight percent of said composition, and said fragrance component is present at about 30 weight percent of said composition.

* * * * *